United States Patent
Cox et al.

(10) Patent No.: US 6,406,847 B1
(45) Date of Patent: *Jun. 18, 2002

(54) MISMATCH REPAIR DETECTION

(75) Inventors: David R. Cox, Belmont; Malek Faham, Daly City; Siamak Baharloo, San Francisco, all of CA (US)

(73) Assignees: The Board of Trustees of the Leland Stanford Junior University, Palo Alto; The Regents of the University of California, Oakland, both of CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,055

(22) Filed: Mar. 17, 1999

Related U.S. Application Data (63) Continuation-in-part of application No. 08/713,751, filed on Sep. 13, 1996, now abandoned.
(60) Provisional application No. 60/004,664, filed on Oct. 2, 1995.

(51) Int. Cl.[7] .......................... C12Q 1/68; C12P 19/31; C07H 21/07; C07H 21/04
(52) U.S. Cl. .................. 435/6; 435/91.2; 536/23.1; 536/24.3; 536/24.31; 536/24.33
(58) Field of Search ................... 435/6, 91.2; 536/23.1, 536/24.3, 24.37, 24.33

(56) References Cited

U.S. PATENT DOCUMENTS

| | | | |
|---|---|---|---|
| 5,376,526 A | 12/1994 | Brown et al. ................... | 435/6 |
| 5,556,750 A | 9/1996 | Modrich et al. ................ | 435/6 |
| 5,679,522 A | * 10/1997 | Modrich et al. ................ | 435/6 |

OTHER PUBLICATIONS

Carraway et al, "Repair of heteroduplex DNA molecules with multibase loops in *E. coli*", Bacteriol. 175(13):3972–3980, Jul. 1993.*
Parker et al., "Repair of DNA heteroduplexes containing small heterologous sequences in *E. coli*", Proc. Natl. Acad. Sci. 89:1730–1734, Mar. 1992.*
Dias et al, "Genetic recombination as a reporter for screening steroid receptor agonists and antagonists", Anal. Biochem. 258:96–102, Apr. 1998.*
Stratagene catalog, p. 39, Jan. 1988.*
Cheung et al, "Genomic mismatch scanning identifies human genomic DNA shared identical by descent", Genomics 47:1–6 (Jan. 1998).*
Bishop and Williamson, "The Power of Identity–by–State Methods for Linkage Analysis," *American Journal of Human Genetics* (1990) vol. 46:254–265.
Brookes, et al., "Cloning the Shared Components of Complex DNA Resources," *Human Molecular Genetics* (1995) vol. 3:2011–2017.
Carraway and Marinus, "Repair of Heteroduplex DNA Molecules with Multibase Loops in *Escherichia coli*," *Journal of Bacteriology* (1993) vol. 175:3972–3980.
Ferrin and Camerini, "Selective Cleavage of Human DNA:RecA–Assisted Restriction Endonuclease (RARE) Cleavage," *Science* (1991) vol. 254:1494–1497.
Grompe, "The Rapid Detection of Unknown Mutations in Nucleic Acids,"*Nature Genetics* (1993) vol. 5:111–117.
Mills, et al., "Electrophoretic Evidence That Single Stranded Regions of One or More Nucleotides Dramatically Increase the Flexibility of DNA," *Biochemistry* (1994) vol. 33:1797–1803.
Modrich, "Mechanisms and Biological Effects of Mismatch Repair," *Annu. Rev. Genet.* (1991) vol. 25:229–253.
Parker and Marinus, "Repair of DNA Heteroduplexes Containing Small Heterologous Sequences in *Escherichia coli*," *P.N.A.S.* (1992) vol. 89:1730–1734.
Raposa, et al., "Some Features of Base Repair Mismatch and Heterology Repair in *Escherichia coli*," *Genetics* (Nov. 1987) vol. 117:381–390.
Wagner and Messelson, "Repair Tracts in Mismatched DNA Heteroduplexes," *P.N.A.S.* (1976) vol. 73:4135–4139.

* cited by examiner

*Primary Examiner*—Jeffrey Fredman
(74) *Attorney, Agent, or Firm*—Pamela J. Sherwood; Bozicevic, Field & Francis LLP (57) ABSTRACT

Mismatch Repair Detection (MRD), a novel method for DNA-variation detection, utilizes bacteria to detect mismatches by a change in expression of a marker gene. DNA fragments to be screened for variation are cloned into two MRD plasmids, and bacteria are transformed with heteroduplexes of these constructs. Resulting colonies express the marker gene in the absence of a mismatch, and lack expression in the presence of a mismatch. MRD is capable of detecting a single mismatch within 10 kb of DNA. In addition, MRD can analyze many fragments simultaneously, offering a powerful method for high-throughput genotyping and mutation detection.

12 Claims, 5 Drawing Sheets

Genomic copy Y sequence

| PCR amplification

| Denature

| Hybridize vectors and Y strand.
| Ligate.

MISMATCH REPAIR DETECTION

CROSS-REFERENCE TO RELATED APPLICATIONS

This application is a continuation-in-part of U.S. patent application Ser. No. 08/713,751, filed Sep. 13, 1996, now abandoned; which claims priority to U.S. Provisional Patent Application No. 60/004,664, filed Oct. 2, 1995.

GOVERNMENT GRANTS

This invention was made with government support under Contract Nos. HD 24610 07-10 and 5T32GM07618 awarded by the National Institutes of Health. The Government has certain rights in this invention.

INTRODUCTION

Background

The detection of mutations in genomic DNA plays a critical role in efforts to elucidate the genetic basis of human disease. For many types of genetic screening and analysis, knowledge of the presence of a mutated copy of a gene is essential. Such information may be used in prenatal and other genetic testing, as well as analysis of tumor cells and other somatic mutations. For many genes, there are a number of different mutations that can affect function.

Common diseases such as diabetes, heart disease and psychiatric disorders are caused in part by genetic variations in multiple genes. Genetic variations are not only involved in the genesis of diseases but they are also chief determinants of disease progression and response to treatment. Identification of the genetic variations involved in common diseases can greatly improve the diagnosis, prognosis, and treatment of such diseases.

One approach for identifying the potentially causative variations involved in common diseases is to screen patients and controls for genetic variations in a large number of candidate genes. Genetic coding sequences constitute less than 5% of the entire human genome, yet the vast majority of human diseases are caused by sequence variation in these coding sequences. Reagents for large scale screening of genes are already available, as a significant proportion of human gene sequences exists in the rapidly expanding public databases. Many DNA variation screening methods have been developed, e.g. single stranded conformational polymorphism (SSCP); and high performance liquid chromatography (HPLC). Since these methods are not designed to screen many genes simultaneously, their usefulness has been limited to testing a handful of candidate genes.

In the absence of high throughput technology capable of large scale screening of genes for the identification of variations involved in diseases, less straight forward approaches such as association and linkage mapping have been proposed. In these approaches, neutral genetic variations (polymorphic markers) are cataloged into a genetic map. These polymorphic markers are used in a genetic linkage or association analysis to approximate the chromosomal location of the disease genes.

Association studies are based on the probability that certain polymorphisms in close proximity to the ancestral disease-causing variation are still present in today's patient population. In linkage or association mapping one hopes that at least a single marker is sufficiently close to the disease-causing variation, and therefore would co-segregate with the disease in a family or in a population. The analysis assumes that a large proportion of the mutations had a single point of origin.

Linkage and association based approaches have been successful for mapping of simple Mendelian diseases. However, mapping of diseases with a complex mode of inheritance has been less successful. Identification of the variations that are involved in such diseases is widely believed to require the performance of association analysis using tens of thousands of markers. Because single nucleotide polymorphisms (SNPs) are the most prevalent polymorphisms, they are proposed to be the markers of choice for these association studies.

Multiple methods, such as chip hybridization and oligonucleotide ligation assay (OLA), have been developed for genotyping of SNPs. All these SNP genotyping methods operate on a common principle of genotyping a previously identified single base polymorphism. Polymorphic sites are first identified by sequencing multiple individuals, then compiled into a map. Finally, patients and controls are tested for the presence or absence of each polymorphism.

In view of the importance of genetic testing, methods whereby one can easily screen for genetic mismatches between two DNA molecules is of great interest. A simple method to determine whether two DNA molecules are identical or different, and that is capable of multiplex analysis would be of great benefit in these analyses.

Relevant Literature

Techniques for detection of conformational changes created by DNA sequence variation as alterations in electrophoretic mobility are described in Orita et al. (1989) *P.N.A.S.* 86:2766; Orita et al. (1989) *Genomics* 5:874; Myers et al. (1985) *N.A.R.* 13:3131 (1985); Sheffield et al. *P.N.A.S.* (1985) 86:231; Myers et al. *Meth. Enzym* 155:501; Perry and Carrell (1992) *Clin. Pathol.* 45:158; White et al. (1992) *Genomics* 5:301. Techniques that use chemicals or proteins to detect sites of sequence mismatch in heteroduplex DNA are described in Cotton et al. (1988) *P.N.A.S.* 85:4397; Myers et al. (1985) *Science* 230:1242; Marshal et al. (1995) *Nature Genetics* 9:177 (1995); Youil et al. (1995) *P.N.A.S.* 92:87. Chip hybridization is described in Wang et al. *Science* 280: 1077–82.

Grompe (1993) *Nature Genetics* 5:111 reviews methods for screening large stretches of DNA. Mapping strategies may be found in Risch (1990) *Am. J. Hum. Genet.* 46:229–241; Lander and Botstein (1987) *Science* 236:1567–1570; and Bishop and Williamson (1990) *Am. J. Hum. Genet.* 46:254–265. Sandra and Ford, (1986) *Nucleic Acids Res.* 14:7265–7282 and Casna, et al. (1986) *Nucleic Acids Res.* 14:7285–7303 describe genomic analysis.

However, several approaches are presently available to isolate large DNA fragments, including long range PCR with enzymes with high fidelity described in Nielson et al. (1995) *Strategies* 8:26; recA-assisted cleavage described by Ferrin and Camerini-Otero (1991) *Science* 254:1494; and the use of a single set of oligonucleotide primers to PCR amplify multiple specific fragments simultaneously in Brookes et al. (1995) *Human Molecular Genetics* 3:2011.

The *E. coli* methyl mismatch repair system is described in Wagner and Messelson (1976) *P.N.A.S.* 73:4135; Modrich (1991) *Annu. Rev. Genet.* 25:229; Parker and Marinus (1992) *P.N.A.S.* 89:1730; and Carraway and Marinus (1993) *J. Bacteriology* 175:3972. The normal function of the *E. coli* methyl-directed mismatch repair system is to correct errors in newly synthesized DNA resulting from imperfect DNA replication. The system distinguishes unreplicated from newly replicated DNA by taking advantage of the fact that methylation of adenine in the sequence GATC occurs in unreplicated DNA but not in newly synthesized DNA. Mismatch repair is initiated by the action of three proteins, MutS, MutL and MutH, which lead to nicking of the unmethylated, newly replicated strand at a hemimethylated GATC site. The unmethylated DNA strand is then digested and resynthesized using the methylated strand as a template. The methyl-directed mismatch repair system can repair single base mismatches and mismatches or loops of up to four nucleotides in length. Loops of five nucleotides and larger are not repaired.

The use of site specific recombinases in eukaryotic cells is described by Wahl et al., U.S. Pat. No. 5,654,182; and by Sauer, U.S. Pat. No. 4,959,317.

SUMMARY OF THE INVENTION

Compositions and methods are provided for an in vivo bacterial assay, termed "Mismatch Repair Detection" (MRD). The method detects mismatches in a double stranded DNA molecule, where the sequence of one strand differs from the sequence of the other strand by as little as a single nucleotide. The two strands of the DNA molecule are from different sources. One strand is unmethylated DNA, having a detectable marker gene and the sequence being tested for mismatches. The other strand is methylated DNA, having an inactivated copy of the marker gene where the defect does not activate repair mechanisms, and another copy of the sequence to be tested. Heteroduplex dsDNA formed from the hybridization of the two strands is transformed into a bacterial host with an active methyl mismatch repair system (MMR host).

The host repair system is activated by a mismatch in the sequence of interest, and will then "co-repair" the marker gene, to produce an inactive, double stranded copy. When the two strands of the sequence of interest are a perfect match, the marker gene is not altered, and the transformed bacteria will produce active marker. Where a mismatch is present, the transformants are readily identified by the lack of active marker, and may then be isolated and grown for further analysis. MRD is a rapid method for analysis of numerous fragments simultaneously. It is useful as an assay for enumerating differences between various sources of DNA, and as a means of isolating DNA with variant sequences.

DESCRIPTION OF THE SPECIFIC EMBODIMENTS

Mismatch Repair Detection (MRD) is a method of detecting mismatches in the sequence of a double stranded DNA molecule. The method will determine whether two DNA sequences differ by as little as a single base change, in a region of over 10,000 nucleotides. Multiple DNA fragments can be analyzed in a single reaction, and the process is easily scaled up to run large numbers of reactions in parallel. Depending on the input DNA, MRD can be used for various purposes. It is used in genetic mapping by testing a large number of polymorphic markers in order to analyze large regions of eukaryotic chromosomes for the presence of mutations. In a large pool of genomic or cDNA clones, the method will identify those DNAs where there is a mismatch between the control and test population, providing a particularly simple method of isolating variant alleles from a particular locus or region. The method can also be used to detect somatic changes in DNA, such as those found in tumor cells, or in the hypermutation of antibody genes. A key advantage of MRD is that, once provided with suitable vectors, the procedure is extremely easy to perform.

The ability to perform high throughput DNA variation detection makes Mismatch Repair Detection (MRD) ideal for performing association and direct screening studies. MRD's multiplexing potential exceeds that of currently known methods, therefore offering an improvement over other methods for large scale SNP genotyping.

MRD also can be used to screen a massive number of candidate genes in order to identify disease-causing variations. It is possible to test the coding regions of all human genes in a limited number of MRD reactions. Testing the coding regions of all the genes in a population of patients and controls will readily reveal disease-causing variations. Sensitivity of this direct approach is significantly higher than that of the association studies as it does not require assumptions as to the origin of mutation and the prevalence of the disease-carrying ancestral chromosome in the patient population. Methods detecting disease-causing variations directly are more likely than association methods to succeed in identifying these variations. This direct candidate gene screening approach is powerful and effective and can greatly accelerate the identification of variations causing clinically-significant phenotypes, greatly improving disease diagnosis, prognosis, and treatment.

Applications of the method based on direct screening of disease genes include diagnosis; sub-diagnosis where one distinguishes between mutations in two related disease associated genes, e.g. factor VIII vs. factor IX deficiency; prognosis of disease susceptibility; treatment development; and treatment optimization.

MRD Method

Mismatch Repair Detection (MRD) utilizes *Escherchia coli's* ability to recognize mismatches in order to detect DNA variations. Many DNA fragments carrying a potential mismatch can be introduced simultaneously into the same *E. coli* culture. Each cell functions as a separate mismatch detection entity. Separation of cells that detected mismatches from those that did not provides two pools of cells containing fragments—one pool with and one without mismatches. The complex process of variation detection is then reduced to the relatively simple task of identifying the DNA fragment content of each pool.

*E. coli* detects single point mismatches as well as one-, two-, and three-nucleotide loops, but it does not detect loops of 5 nucleotides or more. The template for repair by *E. coli* is a hemimethylated double stranded DNA Mismatches in the hemimethylated DNA activate *E. coli's* mismatch repair pathway and result in a large portion of the unmethylated strand (if not its entirety) being degraded and the methylated strand serving as a template to be recopied.

MRD exploits the ability of bacterial cells to "co-repair" long stretches of DNA. When the two strands of a dsDNA molecule have a mismatch, i.e. the nucleotides at a specific position are not complementary, the methyl-directed mismatch repair system of a bacteria will excise and replace the incorrect nucleotide. The strand of DNA that contains within it the modified sequence motif GA$^{methyl}$TC is recognized by the repair system as the "correct" sequence. Correction is initiated by mismatches of one to four contiguous nucleotides. A loop of 5 or more mismatched nucleotides is not recognized by the proteins responsible for initiation of repair, and will remain uncorrected in the absence of other mismatches. However, if repair is initiated at one site on the DNA molecule, then a region extending for at least 10 kb will be co-repaired on the molecule.

The subject method uses a two vector system where each vector contributes one strand to the double stranded test vector. One contributing vector contains a gene encoding an active, detectable marker. For convenience, this will be referred to as the "A vector", or the "standard". The second contributing vector is substantially complementary to the A vector, except that the marker gene has an inactivating insertion, deletion or substitution loop of at least about 5 nucleotides in length. This vector will be referred to as the "I" vector. The A vector and the I vector may be replicated as double stranded DNA, which is then denatured to form single strands, or the vectors may be grown as single stranded entities. The A vector will be replicated under conditions that do not methylate adenine at the GATC recognition site, whereas the I vector will be modified to have methylated adenine at these sites.

One strand from the A vector and one strand from the I vector are annealed to form a heteroduplex, double stranded "A/I" vector. The A/I vector will be methylated on only one strand, e.g. the strand that is contributed by the I vector. When the A/I vector is transformed into a suitable bacterial host having an active methyl mismatch repair system (MMR host), the loop between the active and inactive marker gene will not initiate repair. Correction of the marker gene will only take place when there is a mismatch capable of initiating repair elsewhere in the molecule.

The A/I vector is ligated to a "test sequence". The test sequence is a double stranded DNA molecule comprising the sequence of interest, which is being tested for mismatches. A mismatch in the test sequence will initiate repair of the loop in the marker gene in the bacterial host cell. Each strand of the test sequence is contributed by a different source, herein termed X and Y strands. One or both of the X and Y strands may be ligated to the A and I vectors prior to the previously described annealing step. In one embodiment of the invention, the A vector is ligated to the test sequence, and replicated as a single stranded "standard" vector. Alternatively, the X or Y strand(s) is ligated to the double stranded A/I vector. The A/I vector ligated to the test sequence shall be referred to as the test vector.

Figure 1:
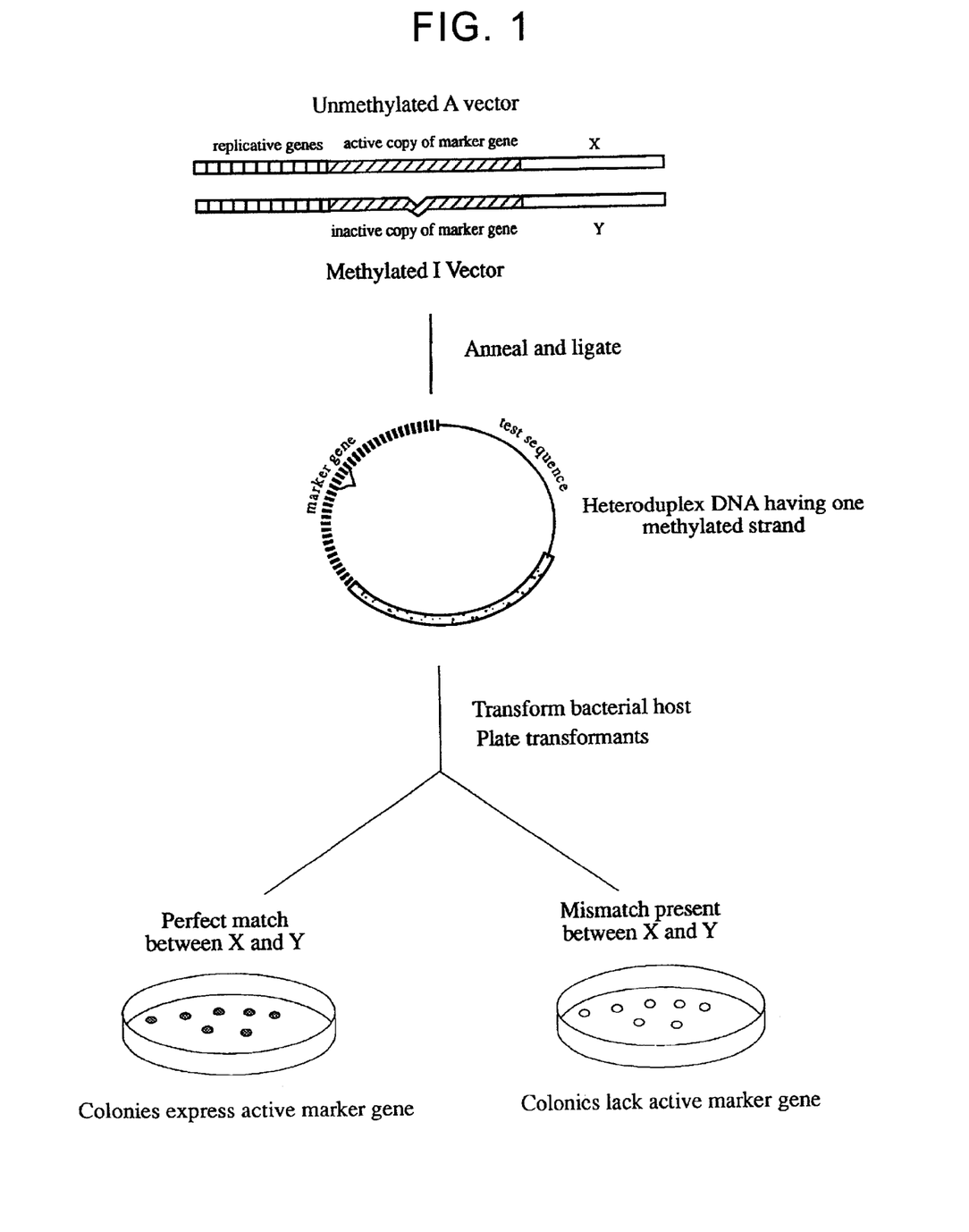
FIG. 1 depicts the method for mismatch repair detection.
Figure 2:
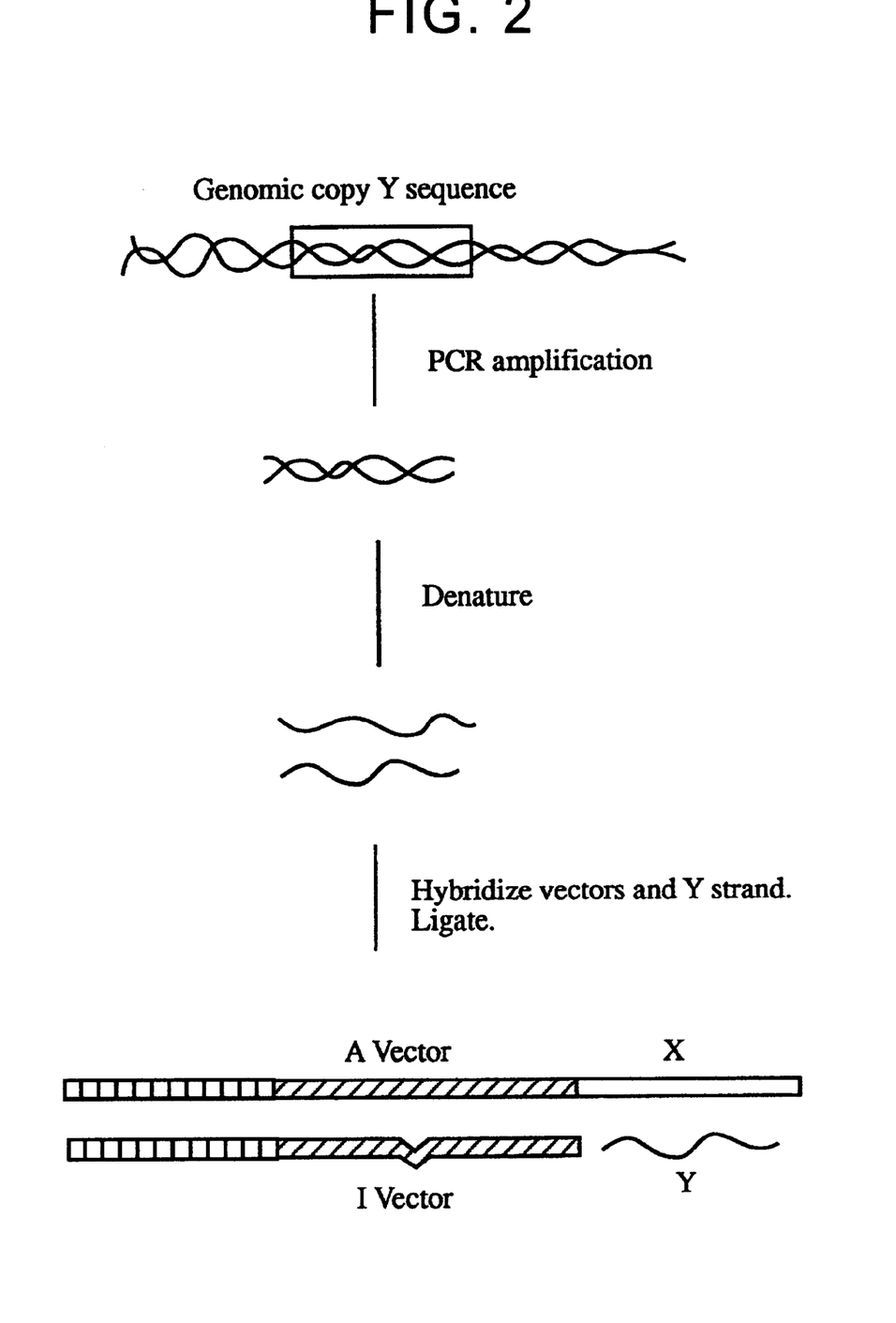
FIG. 2 depicts the method using single or double stranded vectors and an amplification product as a test sequence.

When the X and Y strands of the test sequence are perfectly complementary, then bacteria transformed with the test vector will not initiate correction of the loop in the marker gene, and will express a mixture of the active and inactive marker. If X and Y are mismatched, then repair is initiated. The marker gene will be "corrected" by co-repair, so that both strands will have the inactive marker sequence. Transformed bacteria will therefore lack active marker. The transformed bacteria are grown on plates, liquid culture, etc., under conditions where expression of the marker can be detected. The presence of transformants that lack the marker indicates a mismatch in the test sequence. These transformants may then be isolated for further use. FIG. 1 is a schematic depicting this process.

DNA Vectors

The A and I vectors may be any double stranded or single stranded episomal DNA element that is replicated in the MMR bacterial host, e.g. phage, plasmids, bacterial artificial chromosomes (BACs), etc. Many vectors are known in the art and are commercially available. The two vectors are substantially complementary if single stranded, and substantially identical if double stranded, except for the previously discussed loop in the marker gene, and optionally, the X or Y sequence of interest. Double stranded vectors must be linearized and denatured prior to formation of the A/I vector. The vectors will contain at least one methylation recognition sequence, generally GATC, more usually multiple recognition sequences will be present.

The A and I vectors have an origin of replication that is active in the MMR host cell. The origin may provide for a high or low copy number of the vector. Optionally, the vectors will include a gene encoding a selectable marker, e.g. antibiotic resistance; genes or operons that complement a metabolic defect of the MMR host; resistance to phage infection, etc. Phage vectors may include packaging signals, genes encoding phage coat proteins and regulatory genes, etc. Desirably, the vector will contain a polylinker having a number of sites for restriction endonucleases to facilitate cloning.

The detectable marker gene may be any gene expressed in the bacterial host that provides a directly or indirectly detectable characteristic. Directly detectable markers of interest include antibiotic resistance, color change of a substrate, expression of luciferase, etc. In one embodiment of the invention, the marker is a recombinase, e.g. cre recombinase, FLP recombinase, pSR1 recombinase, etc., which is indirectly detected. For example, the presence of active cre may be detected by recombination between two or more heterologous recombination sites, where a directly detectable marker is present between these recombination sites. The active enzyme will recombine between the sites, thereby deleting the directly detectable marker; while in the presence of inactive enzyme the directly detectable marker is maintained. Such directly detected markers need not be present on the actual vector, and may be contained on the bacterial chromosome or on another episome.

The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences; recombination mediated by Cre enzyme; frt sequences (Golic et al. (1989) Cell 59:499–509; O'Gorman et al. (1991) Science 251:1351–5; recombination mediated by the FLP recombinase), the recognition sequences for the pSR1 recombinase of Zygosaccharomyces rouxii (Matsuzaki et al. (1990) J. Bacteriol. 172:610–8), and the like.

Sequences encoding lox sites are of particular interest for use in the present invention. A lox site is a nucleotide sequence at which the gene product of the cre gene, catalyzes site-specific recombination. A particularly preferred lox site is a loxP site. The sequence of loxP, which is 34 bp in length, is known and can be produced synthetically or can be isolated from bacteriophage P1 by methods known in the art (see, e.g. Hoess et al. (1982) Proc. Natl. Acad. Sci. USA 79:3398). The loxP site is composed of two 13 bp inverted repeats separated by an 8 bp spacer region. The nucleotide sequences of the insert repeats and the spacer region of loxP are as follows:

SEQ ID NO: 1 ATAACTTCGTATA ATGTATGC TATACGAAGTTAT

Other suitable lox sites include loxB, loxL, and loxR, which can be isolated from E. coli (Hoess et al. (1982) Proc.

*Natl. Acad. Sci.* USA 22:3398). The nucleotide sequences of the insert repeats and the spacer region of loxC2 are as follows:
SEQ ID NO:2 ACAACTTCGTATA ATGTATGC TATACGAAGTTAT The heterologous recombination sites useful in the present invention may be either a naturally-occurring sequence or a modified sequence. For example, PCT published application no. WO 93/19172 describes phage vectors in which the VH10 genes are flanked by two loxP sites, one of which is a mutant loxP site. Lox sites can also be produced by a variety of synthetic techniques which are known in the art. For example, synthetic techniques for producing lox sites are disclosed by Ogilvie et al. (1981) *Science,* 210: 270.

Other examples of indirectly detected markers include regulatory factors, e.g. a repressor in an strain constructed to carry one or more genes that are regulated by the specific repressor. Another example of a gene that can have indirect effect on one or more directly detected markers is the amber suppressor supF (or ochre, or opal suppressor).

The use of markers that provide for a color change may be detected by growing the transformed bacteria on medium that allows for the color change, but where the active marker is not required for growth. Transformants expressing the marker are then detectable by visual inspection, spectrophotometry, flow cytometry, etc. Another example of a directly detected marker is a gene that can be expressed on the surface of the bacterium and can therefore be detected by antibodies to it. The use of antibiotic resistance as a detectable marker, e.g. expression of β-lactamase, etc. may require duplicate plates to isolate the mismatched sequence. Alternatively, an antibiotic resistance and an antibiotic sensitivity gene may both be present. For example, the vector may contain a streptomycin sensitivity and a tetracycline resistance gene. When both active genes are present, then cells may be grown in duplicate cultures, one containing streptomycin, and the other containing tetracycline. In another example, transformants are grown under non-selective conditions, and a duplicate plate grown under selective conditions. The colonies that cannot grow in the presence of the antibiotic have a mismatched test sequence. A convenient marker is the LacZα gene, which permits the induction of β-galactosidase expression in the presence of isopropyl-β-D-thiogalactoside (see Messing, supra.). The β-galactosidase cleaves indolyl-β-D-galactoside to produce a colored product.

The inactivated marker gene on the I vector has an insertion, deletion or substitution "loop" of at least about 5 nt. The minimum size of the loop is required because the loop must not initiate repair by the MMR host. Larger loops, of as much as several hundred bases, may be introduced, but are not necessary for the practice of the invention. The loop inactivates the marker gene by introducing a frameshift, stop codon, etc.

In most cases, the I vector will provide the methylated strand. This is done so that during co-repair, the marker gene will be converted to the inactive form. For a number of markers, the active gene is dominant over the inactive. For example, a transformant containing one active antibiotic resistance gene and one inactive gene will be able to grow under selective conditions. Under these same conditions, one can easily distinguish inactive marker from mixed active/inactive. It will be understood by one of skill in the art that this type of a qualitative analysis is merely a convenience, and not essential to the practice of the invention. Methods of quantitative analysis, e.g. ELISA, RIA, etc., that can distinguish between the amount of marker produced by one active gene and the amount of marker produced by two active genes (or multiples thereof) may also be used. Such quantitative methods permit either the detection of cells having only active marker from cells having a mixture of active and inactive, or the detection of cells having only inactive marker from cells having a mixture of active and inactive.

The I vector, which is methylated on the adenine of the GATC recognition site, can be replicated in most common laboratory strains of *E. coli*. Other bacterial hosts that modify DNA at this site may also be used for preparing the I vector DNA. Generally, DNA replicated in non-bacterial cells will require an additional ex vivo methylation step, using purified DNA methylases. Substantially all of the GATC sites in the I vector will be methylated.

The A vector must be replicated in a host that lacks this DNA modification system. Suitable *E. coli* dam– strains include JM110, described in Janisch-Perron (1985) Gene 33:103–119. A vectors replicated in non-bacterial host cells, e.g. yeast, mammalian cell culture, etc. may also be used.

Convenient vectors for preparation of single stranded DNA are derivatives of M13 phage, see Messing (1983) *Meth. in Enzym.* 101:20. M13 is a filamentous bacteriophage, and is commonly used in research laboratories. Derivatives of the wild-type phage are known in the art, and commercially available from a number of sources. M13 phage (+) strand DNA can be isolated from phage particles. Double stranded phage DNA is isolated from infected cells, and the (−) strand can be isolated from the double stranded form by various strand separation methods known in the art, e.g. columns, gels. Alternatively, the (+) strand may be used in combination with the double stranded form. *E. coli* strains suitable for M13 replication include JM101, JM105, JM107, JM109, etc. Vectors carrying the M13 origin of replication (phagemids) and capable of producing single stranded or double stranded DNA are known in the art and widely available.

The strands of the A and I vector that participate in forming the test vector are substantially complementary. To form the test vector, the A and I vectors are linearized, denatured if necessary, and annealed to each other. Various methods are known for linearizing molecules, e.g. digestion with restriction enzymes, etc. Methods of denaturing and annealing DNA are well known in the art, and need not be described in detail. The two termini may have blunt ends, or complementary overhanging ends. The annealed, heteroduplex DNA is circularized by a ligation reaction, using any suitable ligase, e.g. T4, *E. coli*, etc., using conventional buffers and conditions. Generally, the quantity of heteroduplex DNA formed will be sufficient to detect in a standard transformation reaction, e.g. at least about 0.1 picograms of DNA.

Where double stranded vectors are used, the vectors must be linearized and denatured prior to the annealing step. In addition, it is desirable to remove the homoduplex A and I vectors after annealing and prior to transformation, in order to avoid a high background of transformants. One convenient method of performing this step takes advantage of the differential methylation of the two vectors. Restriction enzymes are known in the art that will cleave homoduplex unmethylated DNA, e.g. Mbo I, and homoduplex methylated DNA, e.g. Dpn I, but will not cleave heteroduplex DNA having one methylated and one unmethylated strand. The double stranded A and I vectors are denatured, combined, and reannealed, leaving a mixture of homoduplex DNA (A vector, I vector) and heteroduplex DNA (A/I vector). The mixture is then treated with the methyl specific restriction enzymes. The homoduplex DNA is cleaved, and the heteroduplex is not. The heteroduplex DNA is then used in subsequent steps of the method.

The Test Sequence

The test sequence is a heteroduplex of X and Y, as previously described. X and Y are substantially complementary, and anneal with each other. Generally, the sources of the X and Y strands will be closely related, e.g. individuals of a single species, individuals of closely related species, germline and somatic tissue from a single individual, inbred strains of a species, etc. The test sequence may be derived from any source, e.g. prokaryotic or eukaryotic, plant, mammal, insect, etc. The subject method is particularly useful for the analysis of complex genomes, such as those found in higher plants and animals. The test DNA sequence will usually be of at least about 20 nt in length, and usually not more than about $10^4$ nt in length. The upper limit on length is determined by the ability of the MMR host to co-repair the strand.

In order to initiate co-repair of the marker gene, there must be at least one "initiating mismatch" in the test sequence. An initiating mismatch is a deletion, insertion or substitution of from one to four contiguous nucleotides. A loop of five or more contiguous nucleotides will not initiate repair. Multiple non-contiguous mismatches may be present in the test sequence. Generally, the test sequence will have at least about 90% identity between the two strands. Initiation of co-repair will proceed as long as one initiating mismatch is present.

Various methods may be used to generate the X and Y strands. Isolating and amplifying DNA sequences are known in the art. X and Y may be cDNA from a reverse transcriptase reaction, a restriction fragment from a genome, plasmid, YAC, virus, etc.; an amplification product from polymerase chain reaction (PCR), etc. An important limitation to the use of PCR products is the choice of thermostable polymerase. Polymerases having a 3' to 5' exonuclease activity, e.g. proofreading function, are preferred. Useful thermostable polymerases with proofreading capability that are known in the art include those isolated from *Thermococcus litoralis, Pyrococcus furiosis,* and *Thermus thermophilus*. Commercially available *Thermus aquaticus* polymerase has been found to introduce a significant number of errors into the amplified DNA, and will generally be unsuitable for all but very short, e.g. less than about 500 nt., sequences.

Where the test sequence is obtained from an in vitro amplification reaction, it may be desirable to methylate the amplification product, using conventional enzymes and methodologies.

A number of techniques are known in the art for isolating single strands, or for denaturing double stranded DNA. For example, a reverse transcriptase product may be treated with ribonuclease to leave only the DNA strand. Strand separation gels are known in the art and may be used to separate the two strands of a DNA molecule. PCR may be performed with one primer conjugated to a molecule with a binding partner, such as biotin, haptens, etc. The PCR reaction is then denatured, and bound to a solid substrate conjugated to the binding partner, e.g. avidin, specific antibody for the hapten, etc. The test DNA may be replicated as a single stranded entity, e.g. M13 phage, phagemid, etc. The X and/or Y sequence may be restriction fragments, PCR products, or other double stranded DNA molecules, that are denatured according to conventional methods. International application PCT/US93/10722 describes one method for generating heteroduplex DNA suitable for mismatch testing.

There are several different methods that may be used to attach the test sequence DNA to the vector(s). In one method, the double stranded A/I vector is ligated to double stranded X/Y test sequence DNA. This method ligates double stranded heteroduplex A/I vector to double stranded heteroduplex X/Y test DNA. The two double stranded DNA molecules are combined. It is convenient to have a short, complementary overhang on the termini of the X/Y, and the A/I molecules, such as those formed by digestion with various restriction endonucleases or by the ligation of specific linkers to the termini, where the vector and the test sequence will anneal to each other. Preferably, a different overhang will be present on each termini of one molecule, so as to prevent self-circularization of the vector. Blunt ends may also be used, in which case it may be desirable to phosphatase treat the vector ends to reduce self-circularization. The molecules are ligated to form a circular dsDNA, which is then used in subsequent steps.

In another method, X and Y DNA is ligated into the A and I vectors in a separate cloning step, and the chimeric DNA strands are used to form the A/I heteroduplex molecule. The X and Y sequences may be separately cloned into the A and I vectors, using conventional recombinant DNA methods (see Sambrook et al, supra.). Either strand may go into either vector. The chimeric molecules may then be replicated as previously described, to provide methylated and unmethylated strands. The chimeric molecules are linearized, denatured if necessary, annealed, and ligated as described above to form the A/I vector.

In a preferred method, test DNA from only one source (X) is cloned into the A or I vector, to form a chimeric molecule. While either the I vector or the A vector may be such a chimera, conveniently, the A vector will contain a copy of the test sequence. Such a vector may be referred to as a "standard" vector. A single standard may be used in a reaction, or multiplex reactions may be performed, where a plurality of standards, each comprising a distinct test sequence, are hybridized in a single reaction. The multiplex reaction may combine two or more standards, usually at least about 10 standards, more usually at least about 100 standards, and may combine as many as 10,000 or 100,000 standards.

The single stranded standard vector may be combined in a hybridization reaction with the I vector and the Y test sequence, to form a heteroduplex, where the strand are then annealed and ligated.

In such cases, it will be desirable to clone only one strand of the test sequence into a vector, and have the other strand of the test sequence be provided separately. Using conventional recombinant DNA techniques, the test sequence (arbitrarily designated X) is cloned into the A or I vector. Either vector may be recipient of the X DNA. For some uses of the method, it may be advantageous to use the A vector as recipient, because the final DNA product, after transformation and methyl mismatch repair, will then be corrected to have the sequence of the Y (methylated) strand, thereby allowing isolation and further growth of the Y DNA. If the vector will be grown as a single stranded entity, then the complementarity of the strands must be selected so that X and Y will be capable of hybridizing.

The chimeric A or I vector, containing X DNA, is linearized and annealed to the complementary vector, to form a heteroduplex A/I vector having a single stranded X region. Y DNA is combined with the heteroduplex vector, and annealed to X. It will be understood by one of skill in the art that a single annealing reaction may be performed with these three molecules. Y may be denatured double stranded DNA, e.g. a PCR product, fragment of genomic DNA, etc., or may be single stranded, e.g. cDNA, etc. The three strands (I, AX and Y) are then ligated.

Transformation and Detection

The test vector, heteroduplex A/I vector ligated to X/Y test sequence DNA, is transformed into a suitable bacterial host. Most bacterial species have an active methyl mismatch repair system, and can therefore be used as an MMR host. Suitable species include *E. coli* and other gram negative rods, such as Pseudomonas, Erwinia, Shigella, Salmonella, Proteus, Klebsiella, Enterobacter and Yersinia. Other species of interest include *B. subtilis,* Streptomyces, etc. The genetics and growth requirements of *E. coli* are well known, and in most cases it will be the preferred host. Transformation techniques are well known, for example see Hanahan (1985) in: DNA Cloning, Vol. 1, ed. D. Glover, IRL Press Ltd., 109.

The transformed bacteria are generally grown under selective conditions, where only those cells able to express a vector encoded selective marker can proliferate. Preferably the test vector will include a selective marker, such as antibiotic resistance, for this purpose. The transformants may be grown in a suitable culture medium, e.g. LB broth, SOB broth, 2YT, etc., as a liquid culture, on plates, etc. In some cases, the growth medium will also include any substrates required for showing of the detectable marker.

The determination of transformants expressing active and inactive marker is then made. The method of determination will vary with the specific marker used, as previously discussed. In one embodiment, plates of transformants are counted for colonies having a positive or negative color change, such as cleavage of indolyl-β-D-galactoside to produce a blue color, or expression of luciferase. In another embodiment, replica plates are made, and it is determined whether cells from individual colonies are capable of growing in a selective medium. Transformants grown in liquid culture may by stained, for example with antibodies specific for the selectable marker, and analyzed by flow cytometry to determine the number of cells expressing active marker.

Transformants that lack active marker had an initiating mismatch in the test sequence. An increase in the percentage of transformants that lack active marker, compared to a control, perfectly matched test sequence, is indicative of a mismatch. The transformed bacteria that lack active marker are growing the "corrected" test vector, where both strands of vector DNA will have the sequence of the originally methylated strand. The transformed bacteria that express active marker will generally have a mixture of A and I vector. Vector DNA may be prepared from the transformants, and used for further purification and characterization.

Applications of the Method

The subject method is useful for analysis of DNA polymorphisms, mutation and for isolation of variant sequences. A number of applications for the subject method are based on detection of sequence polymorphisms in a single, known DNA sequence. For example, in prenatal diagnosis one might wish to determine whether a mutation in a particular gene, e.g. hemoglobin, dystrophin, etc., is found in a fetal DNA sample. Many tumor cells contain a mutation in one or more oncogenes and/or tumor suppressor genes. Determining whether a particular gene is altered in a tumor cell sample is therefore of interest. Determining the occurrence and frequency of sequence polymorphisms in a population is important in understanding the dynamics of genetic variation and linkage disequilibrium.

To perform this type of analysis, a control (X) copy of the sequence of interest is cloned into the A or I vector, usually A vector. Where a gene is known to be polymorphic, several different vectors, each having a different allelic form, may be used. The Y sequence is obtained from a suitable source of DNA, depending on the type of analysis being performed. The Y sequence may also be cloned into a vector. In a preferred embodiment, however, a heteroduplex is formed of AX and I strands combined with single stranded Y DNA, where Y may be a denatured PCR product, cDNA etc. X and Y are annealed, and a ligation is performed to produce the test vector.

For genetic testing, one may set up a panel of A or I vectors having defined regions of a chromosome, for example the BRCA1 gene, or CF gene, where a copy of the gene sequence is cloned into the vector. Similarly, for identification of variation involved in clinical phenotypes, one may set up a panel of A or I vectors carrying many fragments to test for SNPs, or gene variations. Due to allelic variation, it may be necessary to compare several sets of control vectors. The length of some genes may necessitate a series of vectors, in order to cover the entire region. The Y sequence DNA is obtained from the individual being tested, using any convenient source of DNA. The Y sequence may be added to the AX/I hybridization reaction, or may be cloned into the I vector in a separate reaction. Hybridization of the panel of X sequence vectors with the corresponding Y sequences may be performed in parallel, or in a multiplex reaction. The presence of specific sequences is then correlated with the presence or absence of active marker gene. One can then determine, for large regions of DNA, or a large number of genes where an individual sequence varies from a standard, control sequence.

The resulting colonies from the above procedure will be a mixture of active marker expressing, having a DNA sequence identical to the control sequence, and lacking active marker, where there was an initiating mismatch in the test sequence. In order to analyze the results, it may be desirable to determine the frequency of these two populations. This may be accomplished by separating the active and inactive colonies into two different pools. Separation may be accomplished by picking colonies, flow cytometry, column separation based on binding of the marker, immunomagnetic bead separation, etc. Vector DNA isolated from these pools is digested with an appropriate restriction endonuclease to release the insert. Gel electrophoresis may then be used to quantitate the amount of insert DNA in each pool, using the vector band as an internal standard, from which the proportion of variant and identical clones can be determined. Acrylamide gels (or other separation methods) can be employed. Alternatively, the insert DNA from each of the pools used as a hybridization probe on a hybridization filter or microarray of fragments corresponding to the fragments being tested. The ratio of signal intensity from hybridization with the active and inactive pool of inserts can be used to determine the proportion of variant and identical sequences. This allows the simultaneous analysis of sequence variation for many different fragments.

The nature of the X/Y sequences varies. In one embodiment the test sequences will include all the coding regions and their regulatory elements for a particular organism, e.g. human, yeast, etc. In another embodiment they are polymorphic markers that can be used for genetic mapping. In yet another embodiment they are one or several genes that are tested in a clinical setting to for the purposes of improving the diagnosis, prognosis, or treatment for a patient.

This multiplexing can be augmented by assessing the genotype of multiple individuals at the same time, for a particular fragment or genetic sequence of interest. Alternatively, multiple samples may be taken from an individual to determine the extent of somatic mutation in a cell population, e.g. tumor cells, etc. The sample nucleic acid may be an amplification product, cloned fragment, etc. By assessing the genetic variation in a population one can estimate the frequency of variation in a particular population in a variety of genes in one experiment. One can identify genes related to clinically relevant phenotypes by identifying those genes that have a higher frequency of variation in the population of interest as compared with the normal population. In addition this approach can be used to identify fragments carrying variations and therefore can be useful as for SNP testing.

In other applications of the method, one may wish to isolate variants of sequences, particularly genomic sequences. In some cases, the control sequence will be only partially characterized. For example, many genetic diseases or conditions are known only by their phenotype and general map position, e.g. a high predisposition to breast cancer, obesity, etc. Localization of the gene to a particular map region, or a YAC clone, still leaves hundreds of thousands of bases of DNA containing the potential gene candidate. MRD provides a means of identifying and isolating the variant sequence.

DNA is isolated from two sources. The DNA may be from a YAC or BAC insert, a restriction fragment from a human chromosome, etc. One source of DNA will have the putative variant sequence, and the other will have the control sequence, e.g. wild-type. Preferably the two sources will be related, e.g. inbred mouse strain, tissue samples from an individual, human parent or sibling, etc. The transformed cells are useful as a source of cloned DNA.

In one method, the two DNA samples are cloned into the I and A vectors, respectively, to provide inserts of not more than about $10^4$ nt in length, and usually at least about $10^2$ nt in length. The vectors are separately replicated in methylation positive and methylation negative conditions, either as single or double strands. The two vectors are then linearized, denatured if necessary, annealed, ligated, and transformed into an MMR host, as previously described. There will be a large number of transformants that represent perfect matches, and will express active marker gene. The transformants that lack an active marker have a mismatch between the two DNA sources, and are candidates for clones of the variant sequence.

The ability of MRD to isolate DNA having a variant sequence can be used in "multiplexing" procedures, where multiple DNA fragments are analyzed in a single reaction. Multiplex reactions may be set up for specific fragments of DNA or regions of a chromosome, etc. In multiplex reactions, generally two cycles of MRD will be performed. The first round of MDR provides a number of bacterial colonies having variant or identical allele(s) from a pool of DNA fragments. The second round of MDR further enriches for the variant sequences.

Regions of DNA may be compared in multiplex reactions. One or many different fragments may be isolated in a single reaction. Generally DNA from one source will be fragmented by a suitable method, e.g. restriction endonuclease digestion, etc., cloned into the appropriate vector, hybridized with the other vector as well as DNA from the other source, and a first round of MRD analysis performed in a single reaction. Colonies having inactive marker after the first round are enriched for variant sequences. DNA isolated from these colonies may be compared to the control sequence, using additional round(s) of MRD to further enrich for variants. The majority of inactive colonies from the second round will carry DNA sequences that differ from the control. Where error prone polymerase was used to generate DNA, the method of "cleaning" described below may be used to enrich for true variants.

An alternative approach to isolating variant sequences is as follows. Two DNA samples, e.g. YAC, plasmid, restriction fragment, etc., containing the region of interest are cleaved with a restriction endonuclease into fragments of not more than about $10^4$ nt. The two samples are combined, denatured, and allowed to anneal. The X/Y mixture is then annealed and ligated into a heteroduplex A/I vector having compatible ends. The mixture is transformed into an MMR host. Any transformants lacking active marker will represent a mismatch between the two DNA sources.

Isolation of variant fragments can be done for many fragments from many people in the same experiment. For example PCR from a pool of individuals can be performed for many fragments. These PCR products can be annealed and ligated into a heteroduplex A/I vector. Alternatively they can be annealed to an A vector with an X sequence already ligated to it. Two MRD procedures might be performed as described above to enrich for the variant fragments. This approach can be useful in identifying in a population the fragments carrying variations and therefore that can be used as genetic markers. In addition this approach may identify variations in coding regions that may be involved in specific clinical phenotypes. This approach can be performed with different populations (one experiment per population) in order to isolate those variations that are specific to a specific population. In other words MRD can be used to identify rare alleles in a population for a large number of genes. An analogous application is the identification of rare alleles produced by somatic mutations or sperms in one individual. Examples of this include identification of rare alleles in a fraction of tumor cells, precancerous changes in a pool of normal cells, mutations caused by environmental mutagens, or somatic mutations that may be relevant in processes such as immune diseases or aging.

In addition to the use of MRD for identification of human genetic variation involved in clinical phenotypes, e.g., phenotypes affecting the development, progression, or treatment of disease, MRD can clearly be used to test variation in nonhuman species. Identification of variations leading to phenotypes in mice, drosophila, yeast and other species is of concern to researchers. In addition, identifying variations in human pathogen like HIV virus of *Mycobacterium tuberculosis* can have important clinical consequences. Finally other uses of MRD can be in identifying variation relevant to farming phenotypes, e.g. variations leading to increased milk production in cows or prolonged freshness in tomatoes.

MRD may be used in conjunction with Taq polymerase to enrich for molecules that are free of PCR-induced errors. Following this "cleaning" protocol, the cloned PCR products is isolated for further analysis. The products of a Taq PCR reaction are cloned into the control and test vectors, and are then hybridized and transformed. The majority of transformants containing Taq PCR-induced errors will present as heteroduplex molecules containing a mismatch and will not produce active marker. In contrast, those PCR products with no PCR-induced errors will contain no mismatches and will produce active marker. These colonies can be isolated, and if desired, undergo a second round of cleansing. A similar protocol may be used to isolate non-variant sequences from a population.

It is contemplated that a kit will be provided for the practice of the subject invention. At a minimum, the kit will contain A and I vectors. The vectors may be single or double stranded. Single stranded vectors may be pre-annealed in an A/I heteroduplex. Competent host bacteria for growing unmethylated and methylated vector may also be included, as well as an MMR host strain. For analysis of specific DNA sequences, e.g. oncogenes, tumor suppressor genes, human β-hemoglobin, cDNA and genomic copies of BRCA1 and BRCA2, a panel covering the human dystrophin gene, etc., a kit may be provided where a chimeric A vector is provided, containing the X (control) sequences. The A and I vector in this case may also be pre-annealed, to form an AX/I heteroduplex. Such a kit may also include specific primers for amplifying the Y sequence DNA, and optionally, thermostable polymerase.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

EXPERIMENTAL

Example 1

Figure 3:
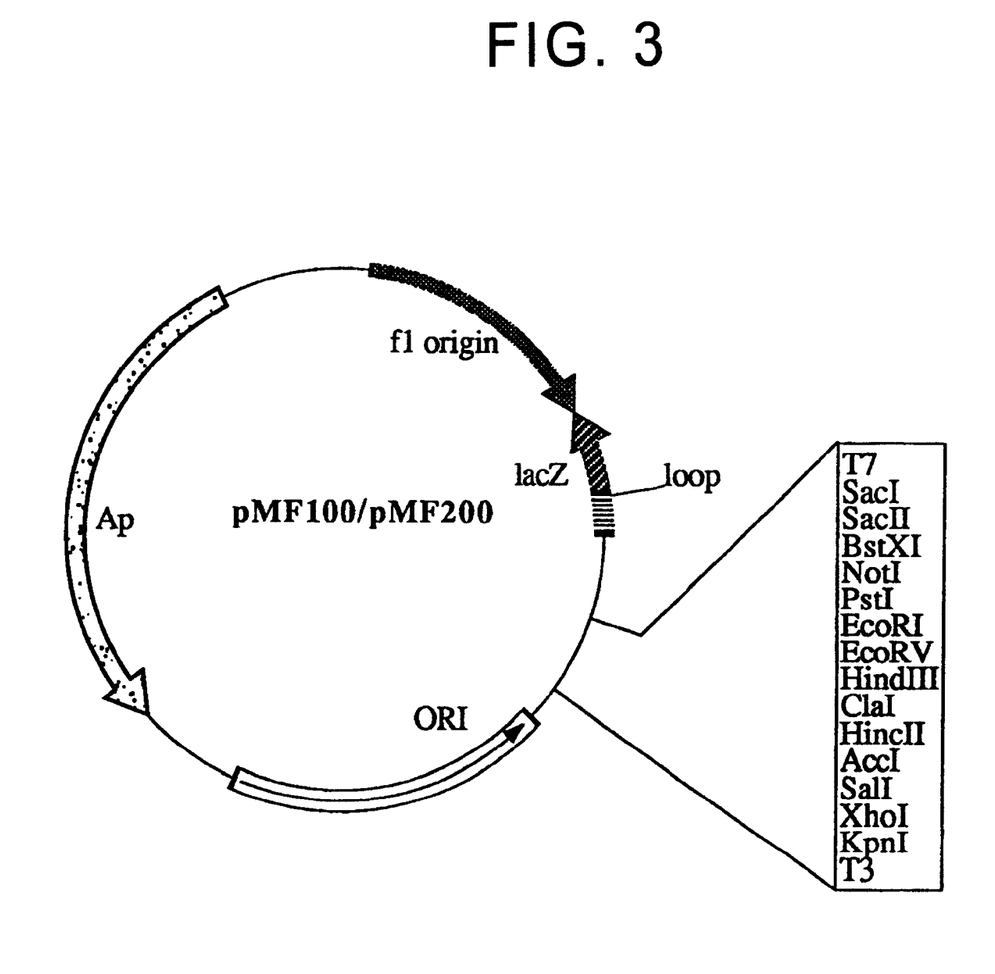
FIG. 3 shows a plasmid map of pMF200 and pMF100.
Figure 4:
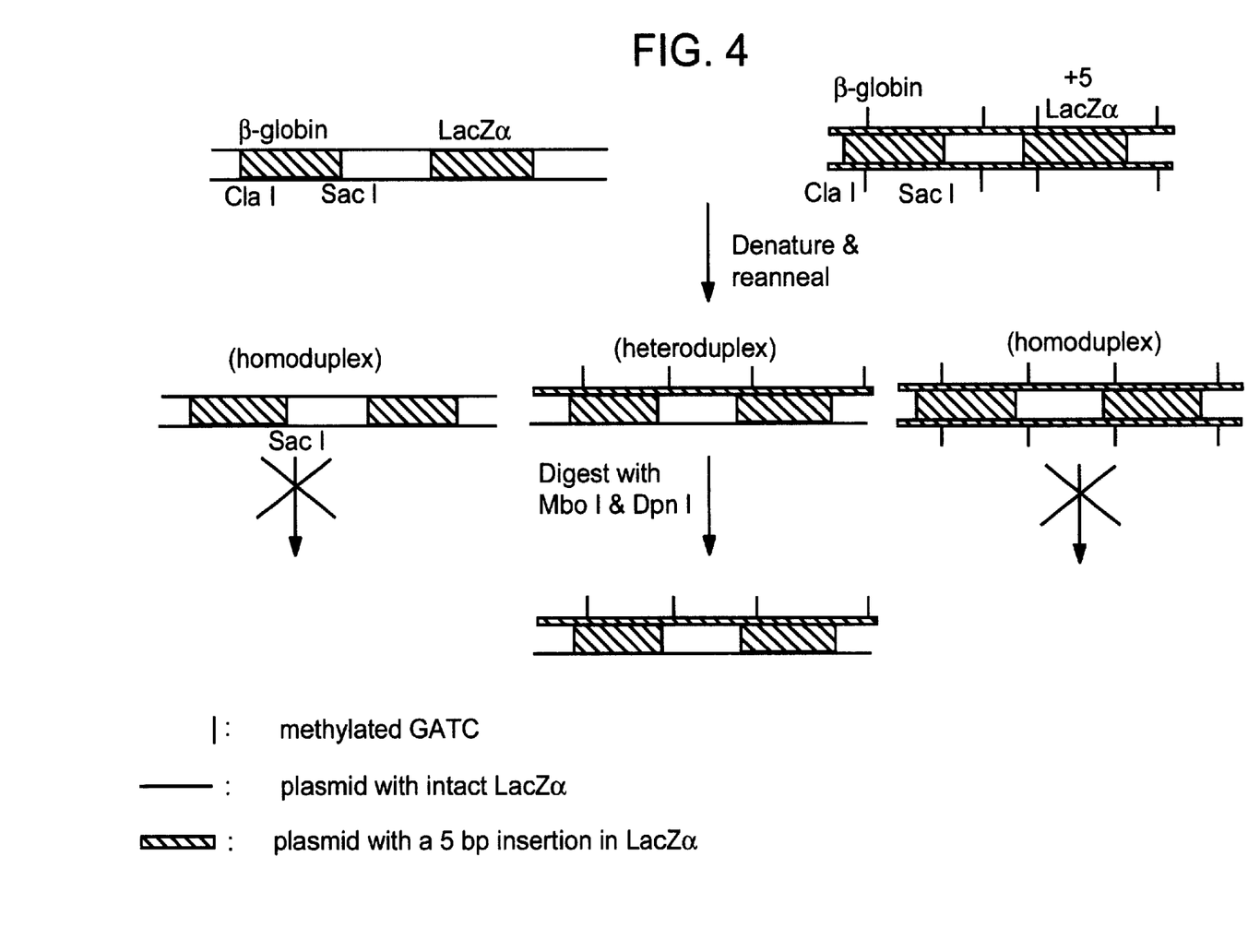
FIG. 4 depicts formation of heteroduplex DNA
Figure 5:
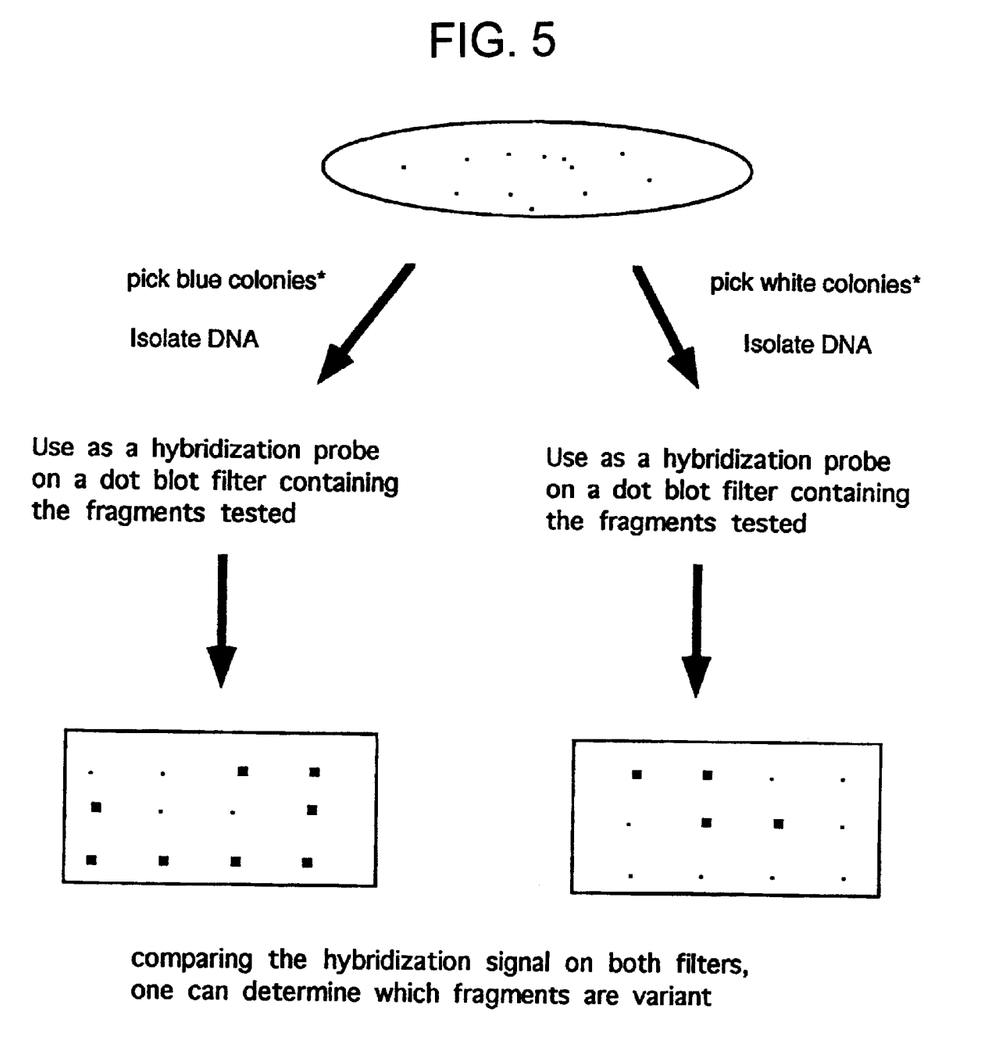
FIG. 5 depicts analysis of MRD results by hybridization.

Two pUC-derived plasmids, the A plasmid (pMF200) and the I plasmid (pMF100), are employed in the MRD procedure. A map of the plasmids is shown in FIG. 3. These plasmids are identical except for a five bp insertion into the Lac Zα gene of pMF100. This insertion results in white colonies when bacteria transformed with the I plasmid are grown on LB plates supplemented with indolyl-β-D-galactoside (Xgal) and isopropyl-β-D-thiogalactoside (IPTG). In contrast, bacteria transformed with the A plasmid result in blue colonies when grown under these conditions.

The initial step of the MRD procedure consists of cloning one of two DNA fragments to be screened for differences into the A plasmid and cloning of the second DNA fragment into the I plasmid. The A plasmid construct is then transformed into a dam– bacterial strain, resulting in a completely unmethylated plasmid while the I plasmid construct is transformed into a dam+ bacterial strain, resulting in a fully methylated plasmid. The two plasmids are then linearized, denatured, and reannealed, resulting in two heteroduplex and two homoduplex plasmids. Following digestion with Mbo I and Dpn I, which digest only homoduplexes, the remaining hemimethylated heteroduplexes are circularized, transformed into *E. coli*, and plated onto agar supplemented with Xgal and IPTG.

In the absence of a mismatch between the two test DNA fragments, the five nucleotide loop in the Lac Zα gene, resulting from heteroduplex formation between the I and the A plasmids, is not repaired by the mismatch repair system. Subsequent plasmid replication produces both I and A plasmids in a single colony, leading to a blue color. In contrast, if a mismatch is present in the heteroduplex DNA, a co-repair event takes place that involves both the mismatch in the DNA as well as the five nucleotide loop in the Lac Zα gene. In this case, the unmethylated Lac Zα gene on the A plasmid is degraded, and replaced by the Lac Zα gene from the methylated strand of the I plasmid, resulting in a white colony. The data show that co-repair of a mismatch and the Lac Zα gene in the MRD system occurs even when the distance between them is greater than 5 kb.

Methods

The MRD vectors. pMF100 and pMF200 are derived from pUC19, with the multiple cloning site displaced from the Lac Zα region. In addition, the MRD vectors contain the Bgl I fragment (2166-472) and most of the multiple cloning site of pBluescript (Stratagene, La Jolla, Calif.). The cloning sites of the MRD vector do not have sites for the restriction endonucleases XbaI, SpeI, BamHI, SmaI and ApaI. The EcoRI site is not unique. pUC19 multiple cloning sites, nucleotides 400–454, were replaced using 70 nucleotide long oligonucleotides with a sequence containing four GATC sites. In addition, the site replacing the pUC19 multiple cloning sites in pMF200 has a 5 bp insertion as compared to pMF100, creating a non-functional Lac Zα in pMF200. The label "loop" in FIG. 3 indicates this difference.

Formation of heteroduplex DNA. DNA from the unmethylated and methylated plasmids are linearized, denatured, and reannealed. The resulting molecules are fully unmethylated A plasmid homoduplexes, fully methylated I plasmid homoduplexes, and hemimethylated heteroduplexes. The mixture is digested with MboI, which digests fully unmethylated DNA, and DpnI, which digests fully methylated DNA. Only the heteroduplex, hemimethylated DNA is left.

Example 2

As an initial test of the sensitivity and specificity of the MRD system, a single nucleotide mismatch was detected in a 550 base pair DNA fragment derived from the promoter of the mouse beta globin gene (Myers et al. (1985) *Science* 229:242). MRD was used to compare this DNA fragment, which contains a T at position −49 (relative to the functional transcription start site of the gene) with a second DNA fragment identical in sequence except for at C position −49. The mismatch was located about 700 base pairs from the five nucleotide Lac Zα loop in the vector. Comparison of the two DNA molecules by using MRD resulted in 90% white colonies. In contrast, comparison of the same two DNA molecules with no mismatch (−49T/−49T), resulted in only 7% white colonies. The data is shown in Table 1.

TABLE 1

Detection of Known Point Mutations using MRD

| Sequence Variation* | Fragment Size | Distance from Loop^ | % White (Inactive) Colonies@ |
|---|---|---|---|
| None[1] | 0.55 | N/A | 7 |
| G_C[1] | 0.55 | 0.7 | 89 |
| A_T[1] | 0.55 | 0.7 | 84 |
| G_T[1] | 0.55 | 0.7 | 82 |
| A_C[1] | 0.55 | 0.7 | 82 |
| C_T[1] | 0.55 | 0.7 | 90 |
| None[2] | 2.0 | N/A | 8 |
| A_C[2] | 2.0 | 0.4 | 35 |
| None[3] | 2.2 | N/A | 10 |
| C_T[3] | 2.2 | 2.3 | 83 |
| G_A[3] | 2.2 | 2.1 | 86 |
| C_T[3] | 2.2 | 1.6 | 81 |
| T_C[3] | 2.2 | 1.8 | 80 |

*A_T variation means that at the only position of variation between the two fragments compared, the dam− grown variant has an A and the dam+ grown variant has a T at the same position on the same strand. Therefore, mismatches produced in such an experiment are A/A and T/T.
^in kilobases.
@At least 250 colonies were counted to determine the percentage.
[1]Experiment using a fragment of the mouse beta globin gene.
[2]Experiment using a fragment of the human agouti gene.
[3]Experiment using fragment of human cystathionine beta synthase gene, at positions 341, 502, 992, and 833, respectively.

Comparison of all possible single nucleotides mismatches at position −49 using MRD revealed proportions of white colonies ranging from 80% to 90%. These results demonstrate that MRD can detect all of the different DNA variations possible at this position with high efficiency.

The MRD system was used to detect a total of five additional single nucleotide mismatches in two different DNA fragments, shown in Table 1. Four of these mismatches are at different nucleotide positions in the human cystathionine beta synthase gene (Kruger and Cox (1995) *Human Molecular Genetics* 4:1155). The remaining one mismatch represent single nucleotide changes in the human agouti gene (Wilson et al. (1995) *Human Molecular Genetics* 4:223). In each case, a single nucleotide mismatch was detected.

A mismatch was detected even when it was as far as 2.3 kb from the Lac Zα loop. Since the proportion of white colonies was greater than 50%, co-repair of the mismatch and the loop on the unmethylated strand occurred irrespective of which side of the mismatch was relative to the loop.

To determine whether the efficiency of mismatch detection would remain high if the distance between a mismatch and the vector loop was even larger, the following experiment was performed. A 9 kb test DNA fragment derived from lambda bacteriophage was cloned into the MRD plasmid system and compared with the same test DNA containing a two base pair insertion located 5 kb from one end of the fragment. Addition of the two base pair mismatch resulted in 70% white colonies, as compared to 10% white colonies in the absence of the mismatch. These results indicate that MRD can detect a mismatch in 10 kb of DNA.

Example 3

MRD was used to detect unknown mutations in genomic DNA fragments generated by the polymerase chain reaction (PCR). PCR is a practical method for obtaining a particular genomic DNA fragment of interest from many different individuals. Recent advances in PCR technology makes it possible to isolate DNA products greater than 10 kb in length (Barnes (1994) *P.N.A.S.* 91:2216; Cheng et al. (1994) *P.N.A.S.* 91:5695). However, the introduction of errors during the PCR reaction severely limits the use of individual cloned PCR products. In an effort to overcome this limitation, an MRD protocol was developed to enrich for molecules that are free of PCR-induced errors. Following this "cleaning" protocol, the cloned PCR products can be compared for DNA sequence differences by using the MRD procedure described above.

The basic principle underlying the MRD cleaning protocol is the fact that any single PCR-induced mutation will make up a very small fraction of all the molecules generated by PCR. As a result, when the products of a PCR reaction are cloned into the A "blue" and the I "white" MRD vectors and assayed as described above, the majority of products containing PCR-induced errors will present as heteroduplex molecules containing a mismatch and will produce white colonies. In contrast, those PCR products with no PCR-induced errors will contain no mismatches and will result in blue colonies. Given that not all mismatches are repaired with 100% efficiency, some blue colonies can be expected to contain PCR-induced errors following the first round of enrichment. However, if blue colonies are isolated and used in a second round of MRD cleaning, those molecules containing PCR-induced errors can be reduced even further. Since each blue colony contains both a blue MRD plasmid and a white MRD plasmid, the second round of MRD cleaning is carried out as follows. Plasmid DNA isolated from blue colonies following the firs round of cleaning is used to transform both dam− and a dam+ bacterial strains. Although both blue and white colonies resulted from each transformation, only the blue colonies are isolated from the dam− transformation, and only the white colonies are isolated from the dam+ transformation. Plasmid DNA is prepared from such colonies and heteroduplexes are isolated as described above. Blue colonies arising from transformation with these heteroduplexes are further enriched for the products free of PCR-induced error. In an experiment in which 75% of molecules contain one or more PCR-induced errors following PCR, assuming 95% efficiency of mismatch repair and 10% frequency of white colonies in the absence of a mismatch, the expectation would be 10% blue colonies following one round of MRD enrichment, with 66% of the molecules in such colonies free of PCR-induced errors. If the plasmid DNA from the blue colonies were used for a second round of MRD enrichment, the expectation would be 41% blue colonies, with 96% of the molecule in such colonies free of PCR-induced errors.

As a test of the practicality as well as the efficiency of the MRD cleaning protocol, a 2 kb human chromosome 21-specific PCR product was isolated from each of the two chromosome 21 homologues of a single individual. The two chromosome 21 homologues were separated from each other in independent hamster-human somatic cell hybrid clones. Genomic DNA isolated from these somatic cell hybrid clones was the source of PCR products. When the PCR products derived from each homologue were compared using MRD as described above, approximately 10% blue colonies were observed in each case.

Following two rounds of MRD cleaning, the proportion of blue colonies as 60–80%, data shown in Table 2. In contrast, when these "cleaned" PCR products derived from the two homologues were compared with each other by using MRD, approximately 90% of the resulting colonies were white, indicating the presence of at least one single base difference in the 2 kb PCR products derived from the two different chromosome 21 homologues. The DNA sequence variation in the PCR products was independently verified by restriction enzyme digestion. These results demonstrate that MRD can be used to enrich for PCR products that are largely free of PCR-induced errors, and that such products can be used in conjunction with MRD to detect human DNA sequence variation.

TABLE 2

Percentage of Inactive Colonies in Different Comparison with Plasmids containing 2 kb PCR Products from two Somatic Cell Hybrids

| Variants Compared* | Percentage of Inactive Colonies[#] |
| --- | --- |
| 1/2 | >90 |
| 2/2 | >90 |
| A1/A1 | 70 |
| A2/A2 | 64 |
| AA1/AA1 | 38 |
| AA2/AA2 | 21 |
| AA1/AA2 | >90 |
| AA2/AA1 | >90 |

*1 and 2 represent products from the two hybrids. 1/1 represents comparison of A vector grown in a dam− strain and containing the PCR product from hybrid 1 to I vector grown in a dam+ strain and containing the PCR product from hybrid 1. A1/A1 represents the comparison of A vector grown in dam− host, obtained from the active colonies of comparison 1/1, to I dam+ grown vectors obtained from the same source. AA1/AA1 represents the comparison of A dam− grown vectors obtained from the active colonies of the comparison A1/A1 to I dam+ grown vectors from the same source. Finally, AA1/AA2 represents the comparison of A dam− grown plasmids obtained from the active colonies of the comparison A1/A1 to I dam+ grown vectors obtained from the active colonies of the comparison A2/A2.

It is evident from the above results that the subject invention provides for an efficient, simple method of detecting mismatches between two DNA sequences. The method provides a means of simply detecting the presence of a mismatch, or can be used to isolate copies of both matched and mismatched DNA. MRD is useful to determining somatic changes in gene sequence, identifying germline mutations for prenatal or other genetic screening, for human gene mapping, and for cloning mutations. A major advantage of MRD is the potential of this system to analyze many fragments simultaneously in a single experiment, allowing the detection of mutations in a region representing hundreds of kilobases of DNA, or for genotyping many loci simultaneously. MRD provides a powerful technique for the detection of unknown mutations, the detection of DNA variation in large genomic regions, and high-throughput genotyping.

Example 4

Use of Cre-Lox as a Detectable Marker

Construction of the Standards

MRD utilizes two vectors that are identical except for a five base pair deletion in the gene coding for Cre recombinase on one of the vectors. DNA fragments are cloned in the vector containing the wild type Cre. These clones, referred to as standards, are made only once and serve as sequence comparison templates for sequences from each person that is to be tested. Standards are grown in an *E. coli* host that is deficient in methylation, and subsequently unmethylated single stranded DNA is obtained.

Heteroduplex Preparation for DNA Variation Screening

In order to perform the screening for DNA variations, DNA fragments that are to be tested are amplified from each individual. After in vitro methylation of the PCR products, single stranded DNA from all of the standards are pooled and added to the tube containing the PCR products. Linearized vector containing the 5 base pair deletion in the Cre gene is also added to the same tube. The three components (the PCR products, the single stranded standards, and the linearized Cre deficient vector) are denatured by NaOH and reannealed by neutralization. This process creates heteroduplexes between the unmethylated single stranded standard, its complementary PCR product and the linearized Cre deficient vector.

Mung Bean nuclease is added to degrade remaining single stranded components. Taq ligase is then added to create closed-circle hemimethylated heteroduplexes. At this point a single tube contains all of the heteroduplexes corresponding to the standards and the gene fragments that are being tested. In a single reaction mixture the heteroduplex DNA is transformed into an electrocompetent *E. coli* strain (Mutation Sorter, MS) engineered to carry on its chromosome a cassette of a tetracycline resistant (tetR) and streptomycin sensitive (strepS) genes flanked by two lox sites.

Separation of Variant and Non-variant DNA Fragments

Those heteroduplex molecules carrying no mismatch (i.e., no variation between the standard and the DNA fragment that is being tested) replicate normally, and plasmids carrying both the active and inactive Cre will be present. The active Cre recombines the cassette between the two lox sites leading to the loss of the tetR and the strepS genes. This renders the cell tetracycline sensitive and streptomycin resistant, and hence it will grow in the presence of streptomycin but not tetracycline.

The presence of a mismatch (i.e., if there is a variation between a standard and the DNA fragment that is tested) in the heteroduplex molecules leads to the repair of such mismatches. In the process of repairing the mismatch the unmethylated strand carrying the active Cre gene is degraded and the strand carrying the inactive Cre is used as a template to be copied. As the result, the cell transformed with a mismatch heteroduplex is devoid of any Cre activity, permitting the cell to retain its tetR and straps cassette and therefore grow in presence of tetracycline and not streptomycin.

By growing the transformation mixture in two tubes containing either tetracycline or streptomycin, fragments containing a variation and those that do not contain a variation are isolated, respectively. The evaluation of DNA variation detection is reduced to identifying which fragments are present in which pools. This task may be done in multiple ways including gel electrophoresis and hybridization.

Identification of Variant and Non-variant DNA Fragments

Using ABI sequencing gels: DNA from each pool is digested with restriction enzymes to release the fragments being tested. Samples of the two restriction digests are fluorescently labeled and run on an ABI sequencing gel. The presence or absence of variation in a fragment is assessed by determining the pool where the specific fragment is present. This can be achieved because the different fragments are separated from each other according to their size.

Using DNA microarray technology: In this procedure all of the fragments that are represented in the standards are dotted onto slides. Subsequently the DNA obtained from the tetracycline containing culture and streptomycin containing culture are fluorescently labeled and used as hybridization probes. The probe from the tetracycline culture hybridizes to the spots corresponding to the DNA fragments that contain variation; the probe from the streptomycin culture hybridizes to the spots corresponding to DNA fragments that contain no variations. Other methods for the analysis of the fragment content of each pool can be utilized, including mass spectroscopy.

In order to achieve the goals of identifying variations involved in clinically relevant phenotypes, many genes need to be tested. This tremendous task is greatly facilitated by MRD's ability to multiplex. Many researchers have used whole cDNA content of the cell as the probe onto a microarray containing more than 10,000 targets. It is therefore be a relatively simple task to use a pool of 4,000 fragments as a probe on a microarray containing 4,000 targets. This will allow for the testing of 4,000 fragments simultaneously, although more samples could be multiplexed. In order to test the entire coding regions of the genes of one human individual, one could test 400,000 fragments with an average size of 300 bp each. It will then take 100 MRD reactions to achieve that task.

Disease-causing variations, by definition, have increased frequency in the patient population than in controls. Since construction of haplotypes and knowledge of every individual's genotype are not necessary to identify the disease-causing variations, patients or controls can be pooled and tested to estimate the frequency of different DNA variations in each population. MRD has the potential to simultaneously estimate the frequency of many variations in a population. First, genomic DNA from many individuals is physically pooled and used as template for subsequent MRD steps. The frequency of every variant fragment is estimated by determining its prevalence in the two pools obtained at the end of the procedure. Obtaining frequencies of different variant gene fragments in different populations, e.g., patients and controls, can quickly identify the fragments carrying disease-causing variations.

In order to demonstrate MRD's potential to multiplex, we have applied the MRD procedure to the identification of DNA sequence variation in 13 DNA fragments randomly selected from a group of published polymorphic Sequence Tagged Sites (STSs). In brief, standards were made for each STS, and heteroduplexes were made between a mixture of the standards and DNA fragments amplified from each individual tested. Heteroduplexes were transformed en masse into the mutation sorter (MS) strain and grown in two separate cultures, one supplemented with tetracycline and the other with streptomycin. DNA from each of the two cultures was fluorescently labeled and loaded on the ABI sequencing machine. Fragment peaks were analyzed and the presence or absence of variations in a particular DNA fragment was assessed by determining the pool where a specific fragment was more prevalent.

The two samples prepared from the cultures supplemented with streptomycin or tetracycline, respectively, have different peak traces. The traces show the different peaks corresponding to the different fragments. Each peak is quantitated automatically. Assignment of the alleles of the tested individual is determined from the relative intensity of a fragment between the two pools. The predominance of a fragment in the streptomycin pool indicates the absence of a variation. In contrast, the predominance of a fragment in the tetracycline pool indicates the presence of a variation on both alleles. Finally, the abundance of a fragment in both pools indicates the individual tested is heterozygous for the fragment. These assignments are reproducible in independent testing. The signal to noise ratio for detecting a heterozygous variation is 10:1; and the detection of homozygous variation is substantially more robust.

The above experiment was performed on a nuclear family of 3 individuals. Each individual was tested three independent times. Variations were detected in all three individuals. Robust signal to noise ratio was obtained; heterozygous alleles were effectively identified with the average signal to noise ratio of 10:1. These results were perfectly reproducible as exactly the same variant fragments were detected in an individual in each of the three independent experiments. Different fragments were variant in the different individuals; the pattern of variation among the three people followed a Mendelian mode of inheritance. In these experiments the sensitivity, specificity and reproducibility of detecting DNA variations by MRD, as well as its potential for high throughput variation screening have been demonstrated.

MRD technology makes the large scale screening of candidate genes for identifying variations that cause common diseases a real possibility. At the heart of this approach lies the ability to identify genomic sequence variations that are more frequent in a particular patient group than the normal population. Identifying these variations can influence many aspects of modern medicine: determining diagnoses, assessing prognoses and devising treatments for human diseases. The knowledge of genetic factors causing common disease will impact medical care in a similar way it has already influenced care for rare simple Mendelian diseases.

What is claimed is:

1. A method of detecting a mismatch between two substantially complementary DNA sequences of interest, the method comprising:
   annealing and ligating a single reaction comprising:
      first vector strands lacking methyl adenine, wherein each vector comprises one of a plurality of distinct sequences of interest, a gene encoding a detectable marker, and an origin of replication active in a bacterial host cell;
      a second vector strand substantially complementary to said first vector and characterized by the presence of methyl adenine at GATC sites, wherein said gene encoding said detectable marker further comprises an inactivating insertion, deletion or substitution of at least 5 nt; and
      a test sequence substantially complementary to said sequence of interest, and suspected of having at least one mismatch of from 1 to 4 contiguous nucleotides in length;
   transforming a bacterial host having an active methyl mismatch repair system with the product of said ligating step;
   determining the presence of bacterial transformants expressing or not expressing said detectable marker;
   wherein the presence of transformants not expressing said detectable marker is indicative of a mismatch between said sequence of interest and said test sequence.

2. The method of claim 1, further comprising isolating and growing said bacterial transformants.

3. The method of claim 1, wherein said test sequence is an amplification product.

4. The method of claim 1, wherein said detectable marker is a site specific recombinase.

5. The method of claim 4, wherein said site specific recombinase is cre recombinase.

6. The method of claim 5, wherein the presence of active cre recombinase is detected by the absence or presence of recombination between two lox sites, wherein directly detected marker is present between said two lox sites.

7. The method of claim 1, wherein said directly detected marker provides for antibiotic resistance or antibiotic sensitivity.

8. The method according to claim 1, further comprising the step of isolating vector DNA from said bacterial transformants.

9. The method according to claim 8, further comprising the step of analyzing the insert DNA in said bacterial transformants to determine the variant and identical DNA sequences.

10. The method according to claim 1, wherein said test sequence is a cDNA.

11. The method according to claim 1, wherein said test sequence of interest is a restriction fragment.

12. The method of claim 1, wherein said detectable marker provides for antibiotic resistance or antibiotic sensitivity.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: lambda phage

<400> SEQUENCE: 1

```
                                                    -continued ataacttcgt ataatgtatg ctatacgaag ttat                                    34

<210> SEQ ID NO 2
<211> LENGTH: 34
<212> TYPE: DNA
<213> ORGANISM: E. coli

<400> SEQUENCE: 2
acaacttcgt ataatgtatg ctatacgaag ttat                                    34
```